(12) United States Patent
Lent et al.

(10) Patent No.: US 7,838,833 B1
(45) Date of Patent: Nov. 23, 2010

(54) APPARATUS AND METHOD FOR E-BEAM DARK IMAGING WITH PERSPECTIVE CONTROL

(75) Inventors: Matthew Lent, Livermore, CA (US); Stanislaw Marek Borowicz, San Jose, CA (US); Mehran Nasser-Ghodsi, Hamilton, MA (US); Niles Kenneth MacDonald, San Jose, CA (US); Ye Yang, Fremont, CA (US); Kenneth J. Krzeczowski, Scotts Valley, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 424 days.

(21) Appl. No.: 11/998,502

(22) Filed: Nov. 30, 2007

(51) Int. Cl.
*G01N 23/00* (2006.01)
(52) U.S. Cl. .................. 250/311; 250/310
(58) Field of Classification Search .............. 250/310, 250/307
See application file for complete search history.

(56) References Cited

U.S. PATENT DOCUMENTS

| | | | |
|---|---|---|---|
| 3,622,694 A | 11/1971 | Liu | |
| 4,421,985 A | 12/1983 | Billingsley et al. | |
| 4,547,702 A | 10/1985 | Schrank | |
| 4,716,339 A | 12/1987 | Roussin | |
| 4,945,237 A | 7/1990 | Shii et al. | |
| 5,576,543 A | 11/1996 | Dingley | |
| 7,041,976 B1* | 5/2006 | Neil et al. | 250/310 |
| 7,141,791 B2* | 11/2006 | Masnaghetti et al. | 250/311 |
| 7,247,849 B1* | 7/2007 | Toth et al. | 250/307 |
| 7,307,253 B2* | 12/2007 | Yamaguchi et al. | 250/310 |
| 7,439,500 B2* | 10/2008 | Frosien et al. | 250/305 |
| 2006/0043294 A1* | 3/2006 | Yamaguchi et al. | 250/310 |
| 2006/0060780 A1* | 3/2006 | Masnaghetti et al. | 250/310 |
| 2006/0226361 A1* | 10/2006 | Frosien et al. | 250/310 |
| 2007/0158567 A1 | 7/2007 | Nakamura et al. | |

* cited by examiner

*Primary Examiner*—Nikita Wells
*Assistant Examiner*—Johnnie L Smith
(74) *Attorney, Agent, or Firm*—Okamoto & Benedicto LLP (57) ABSTRACT

A method of imaging using an electron beam. An incident electron beam is focused onto the specimen surface, a scattered electron beam is extracted from the specimen surface, and a plurality of dark field signals are detected using a detection system. An interpolated dark field signal is generated using the plurality of dark field signals. In addition, a bright field signal may be detected using the detection system, and a final interpolated signal may be generated using the interpolated dark field signal and the bright field signal. User input may be received which determines a degree of interpolation between two adjacent dark field signals so as to generate the interpolated dark field signal and which determines an amount of interpolation between the interpolated dark field signal and the bright field signal so as to generate a final interpolated signal. Other embodiments, aspects and features are also disclosed.

20 Claims, 11 Drawing Sheets

FIG. 1
(Conventional)

ABSTRACT AND METHOD FOR E-BEAM DARK IMAGING WITH PERSPECTIVE CONTROL

BACKGROUND OF THE INVENTION

1. Field of the Invention

The present invention relates to apparatus and methods for electron beam imaging.

2. Description of the Background Art

The two most common types of electron microscopes available commercially are the scanning electron microscope (SEM) and the transmission electron microscope (TEM). In an SEM, the specimen is scanned with a focused beam of electrons which produce secondary and/or backscattered electrons as the beam hits the specimen. These are detected and typically converted into an image of the surface of the specimen. Specimens in a TEM are examined by passing the electron beam through them, revealing more information of the internal structure of specimens.

Bright field imaging and dark field imaging are often used in the context of TEMs. A bright field image may be formed in a TEM by selecting electrons from a central diffraction spot to form the image. A dark field image may be formed in a TEM by selecting some or all of the (non-central) diffracted electrons to form the image. The selection of electrons may be implemented using an aperture into the back focal plane of the objective lens, thus blocking out most of the diffraction pattern except that which is visible through the aperture.

While bright field imaging is commonly used in SEMs, SEMs less commonly use dark field imaging.

SUMMARY

One embodiment relates to a method of imaging using an electron beam. An incident electron beam is focused onto the specimen surface, a scattered electron beam is extracted from the specimen surface, and a plurality of dark field signals are detected using a detection system. An interpolated dark field signal is generated using the plurality of dark field signals. In addition, a bright field signal may be detected using the detection system, and a final interpolated signal may be generated using the interpolated dark field signal and the bright field signal. User input may be received which determines a degree of interpolation between two adjacent dark field signals so as to generate the interpolated dark field signal and which determines an amount of interpolation between the interpolated dark field signal and the bright field signal so as to generate a final interpolated signal.

Another embodiment relates to a scanning electron beam apparatus. The apparatus includes a segmented detector positioned to receive a scattered electron beam to detect a plurality of dark field signals. The apparatus further includes an image processing system configured to generate an interpolated dark field signal using the plurality of dark field signals. In addition, a bright field signal may be detected using the detection system, and a final interpolated signal may be generated using the interpolated dark field signal and the bright field signal. A user control device may be used to determine a degree of interpolation between two adjacent dark field signals so as to generate the interpolated dark field signal and to determine an amount of interpolation between the interpolated dark field signal and the bright field signal so as to generate a final interpolated signal.

Other embodiments, aspects and features are also disclosed.

DETAILED DESCRIPTION

It is desirable to improve and enhance imaging capabilities of SEMs and similar apparatus.

Figure 1:
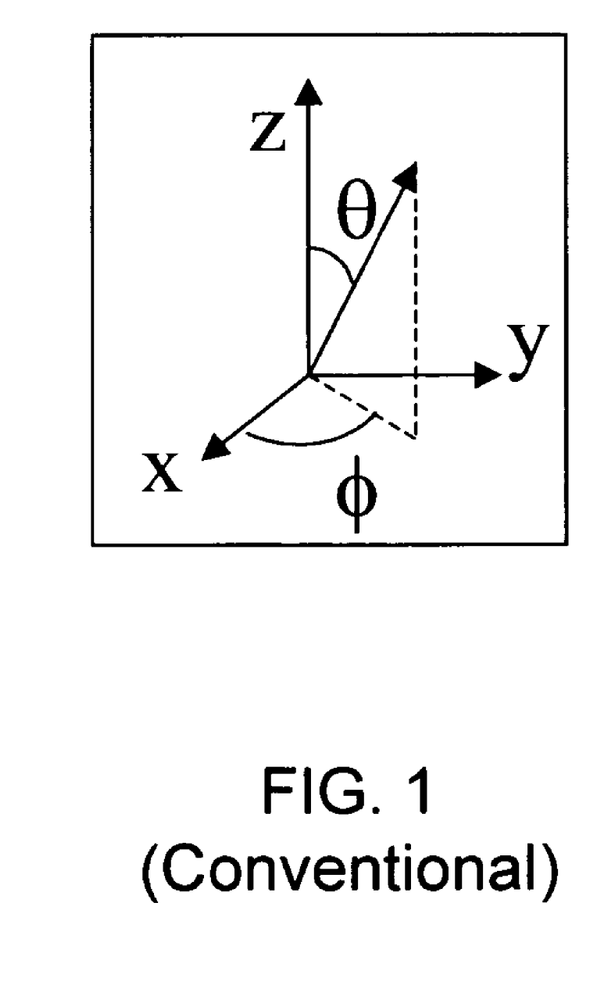
FIG. 1 is a diagram depicting a conventional definition of angles.

FIG. 1 is a diagram depicting a conventional definition of angles. The definitions of the polar angle θ and the azimuth angle φ in relation to scattered electrons emitted from a specimen are shown.

Figure 2:
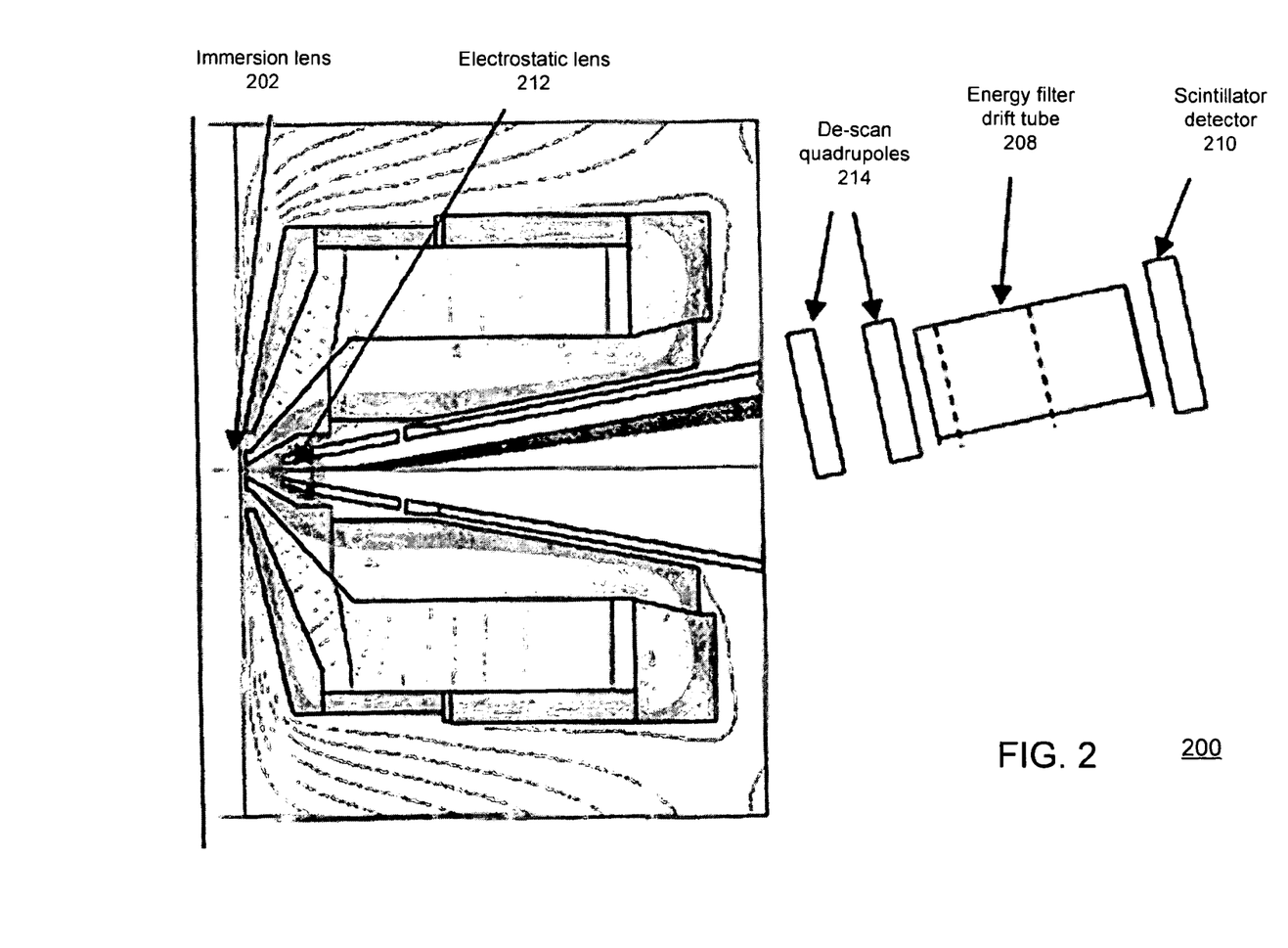
FIG. 2 is a cross-sectional schematic diagram of the SEM dark field imaging system in accordance with an embodiment of the invention.

FIG. 2 is a cross-sectional schematic diagram of the SEM dark field imaging system 200. Depicted are various select components, including an immersion objective lens 202, an electrostatic lens 212, de-scan quadrupole lenses 214, the energy filter drift tube 208, and the scintillator detector 210.

The immersion lens 202 may be configured with a high extraction field so as to preserve azimuthal angle discrimination. However, good polar angle discrimination requires equalizing the radial spread of different energy electrons. Slowing the electrons to their "native" energies for a period of time allows for equalizing the radial spread. This is because the lowest energy electrons would have the longest transit time to allow their radial velocity component to spread them more than the higher energy electrons. The energy filter 208 may be configured to align the secondary electron polar angles across the secondary electron energy spectrum. This may be done by using a drift tube configuration to allow radial spreading of the electrons as a function of their axial energy.

The electrostatic lens 212 is a lens that may be configured to control the imaging path beam divergence. In other words, the strength of the electrostatic lens 212 may be adjusted to control the cone angle of the scattered electrons to preferably keep the cone angle constant. Alternatively, the electrostatic lens 212 may be positioned in the path of the scattered electrons immediately prior to or after the energy filter drift tube 208.

Figure 3A:
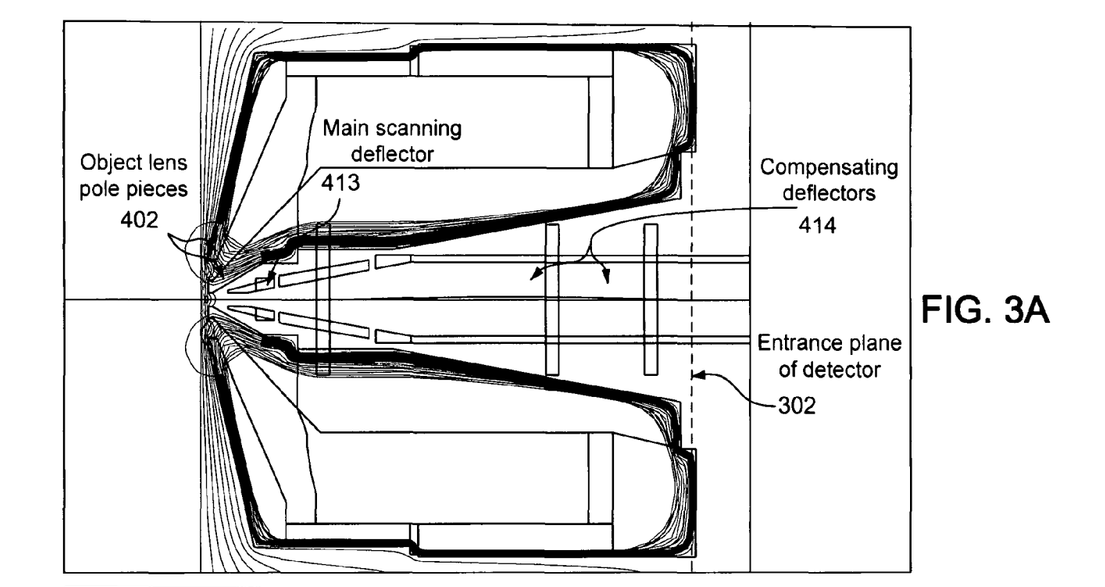
FIG. 3A is a cross-sectional diagram showing the scanning deflectors and compensating deflectors in the SEM dark field imaging system in accordance with an embodiment of the invention.

The de-scan quadrupole lenses 214 comprise compensating deflectors that compensate for the scanning performed by the main scanning deflector 213 (shown in FIG. 3A). In alternate embodiments, the de-scan lenses may comprise octopole, or sextupole, or other multipole lenses. The detector 210 may comprise a YAP scintillator with segmented light pipe.

Figure 3B:
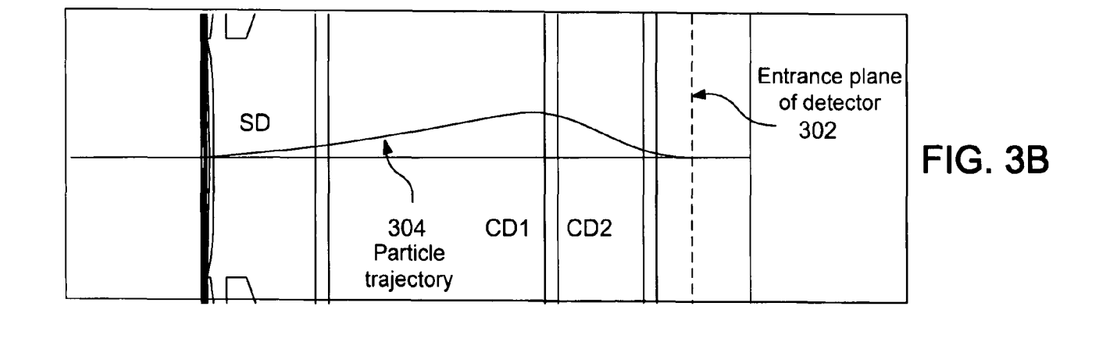
FIG. 3B is a diagram that an electron trajectory in correspondence with FIG. 3A.

FIG. 3A is a cross-sectional diagram showing the scanning deflectors 213 and compensating deflectors 214 in the SEM dark field imaging system in accordance with an embodiment of the invention. FIG. 3B is a diagram of an electron trajectory in correspondence with FIG. 3A. As shown in FIG. 3B, the particle trajectory 304, the electron enters the detector's entrance plane 302 substantially on-axis with little or no radial slope. (In FIG. 3B, the labels "SD", "CD1", and "CD2" indicate the approximate positions of the scanning deflector and the two compensating deflectors, respectively.)

Figure 4A:
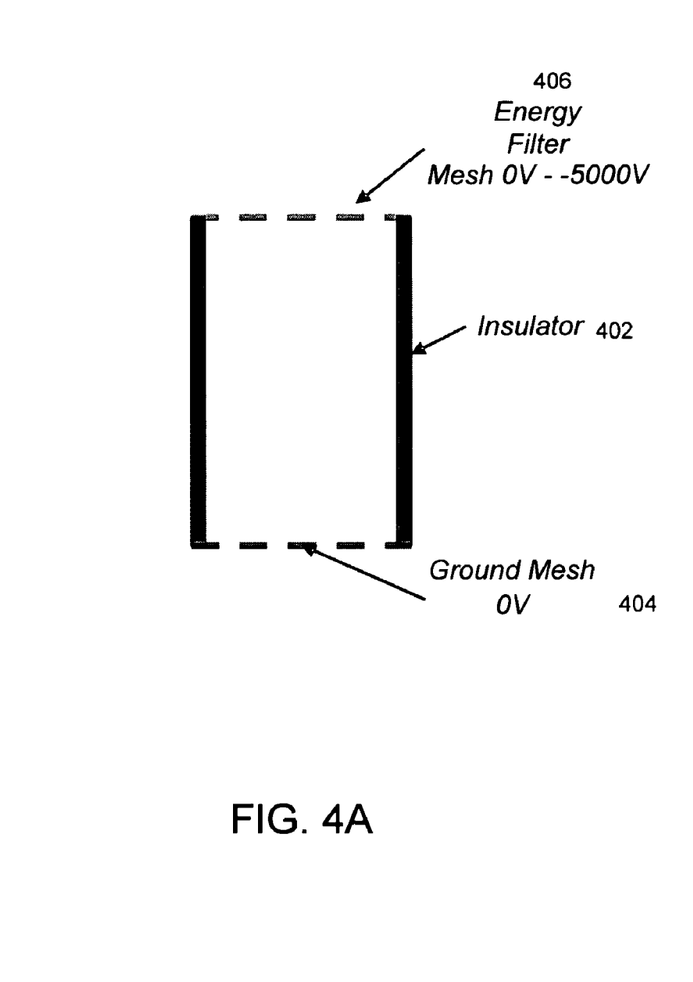
FIG. 4 depicts an energy filter component in accordance with an embodiment of the invention.
Figure 4B:
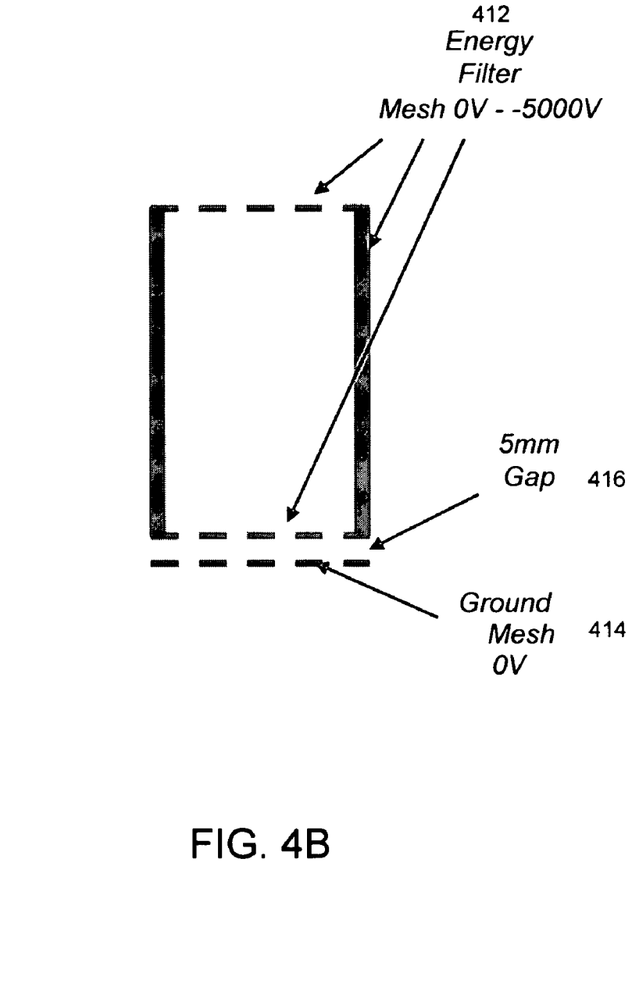

FIG. 4 depicts an energy filter component in accordance with an embodiment of the invention. In this embodiment, the energy filter 208 comprises a conductive or resistive energy filter drift tube 412 whose voltage may be varied, for example, between zero volts and minus 5000 volts. The tube 412 includes meshes on each end that are conductively coupled to the cylinder. In addition, on the detector side of the drift tube 412, there is a small gap 416 separating the tube 412 from a ground mesh 414.

In one embodiment, the voltage on the energy-filter drift tube 412 is set to be at the surface potential of the specimen. This may be done, for example, by a rapid voltage sweep to determine the cut-off voltage at which secondary electrons are no longer detected, followed by backing off the voltage to set the voltage for the energy-filter drift tube 412. This sweep/backoff procedure would be used if the specimen includes insulating portions (such as due to oxide) such that the surface potential is not known. If the surface potential is known (for example, due to the specimen being conductive), then the energy-filter voltage may be simply set ("dialed-in") to that voltage.

Figure 5A:
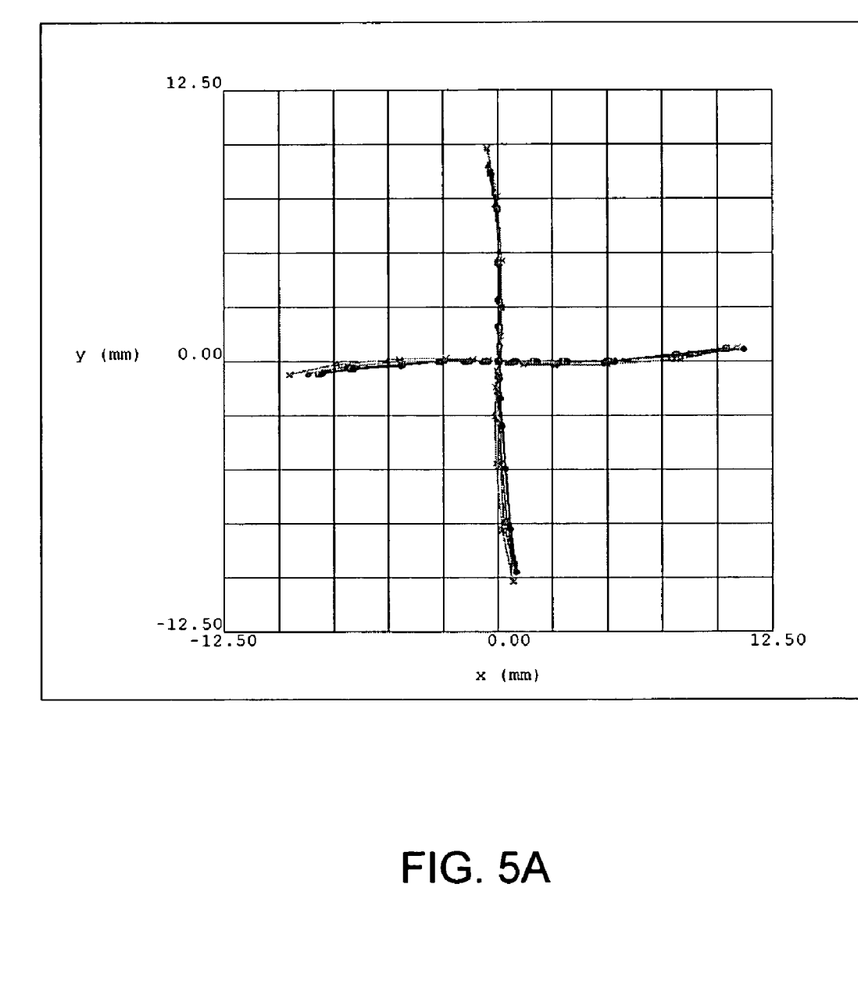
FIG. 5A is a diagram depicting electron landing positions in the plane of the detector for multiple electron energies at different polar angles in accordance with an embodiment of the invention.

FIG. 5A is a diagram depicting electron landing positions in the plane of the detector for multiple electron energies at different polar angles in accordance with an embodiment of the invention. The spot diagram is at the scintillator plate from a simulation including 1, 2, 5, and 10 electron volt secondary electrons. The points associated with each energy are connected together with lines and represent initial polar angles from 0 to 90 degrees in 5 degree increments per quadrant. The plots in each quadrant represent azimuthal angles of 0, 90, 180 and 270 degrees. The spot diagram of FIG. 5A indicates that by segmenting the detector, azimuth and polar angle discrimination may be achieved.

Figure 5B:
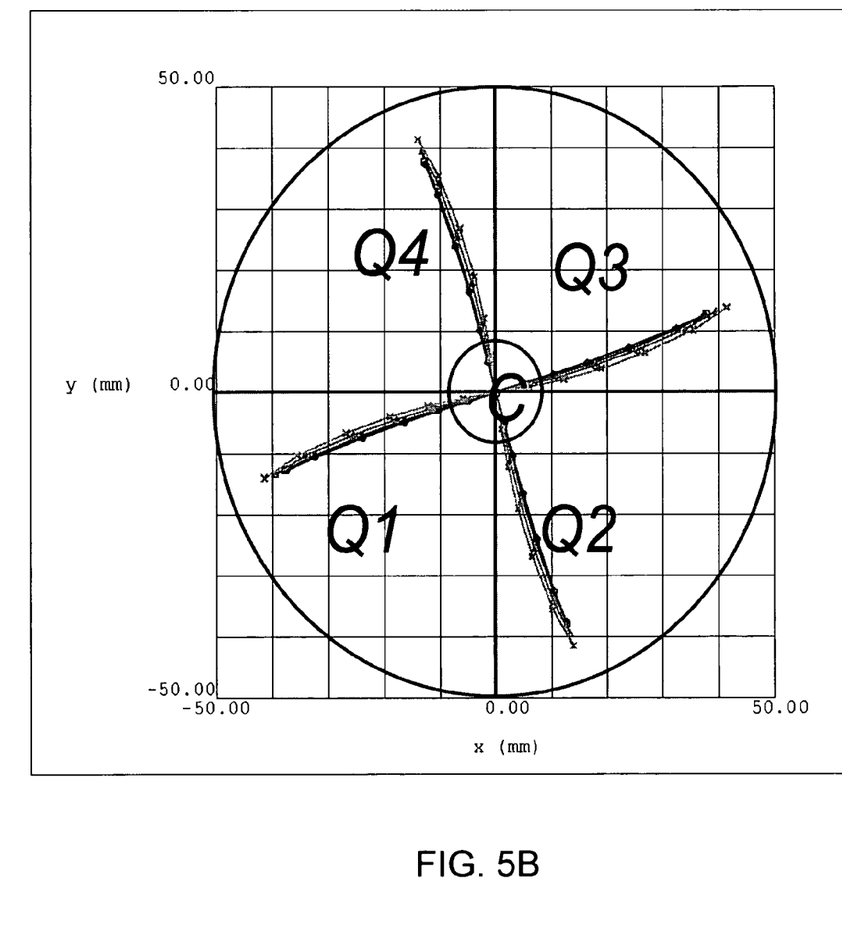
FIG. 5B is a diagram depicting an example detector segmentation in accordance with an embodiment of the invention.

FIG. 5B is a diagram depicting an example detector segmentation in accordance with an embodiment of the invention. The detector design of FIG. 7B is fairly simple, having a center segment C and four outer quadrants Q1, Q2, Q3, and Q4. In one implementation, the construction may be made using a 1" YAP crystal attached to a light-pipe that is segmented as shown in the diagram. Alternatively, a fiber bundle could be used. Five photomultiplier tubes would be used. Bright field and voltage contrast images may be acquired by summing detected data from all detector segments. Images may also be captured using one or more of the outer quadrants, or by calculating difference signals by subtracting one signal (or combination of signals) from another signal (or combination of signals).

Figure 6:
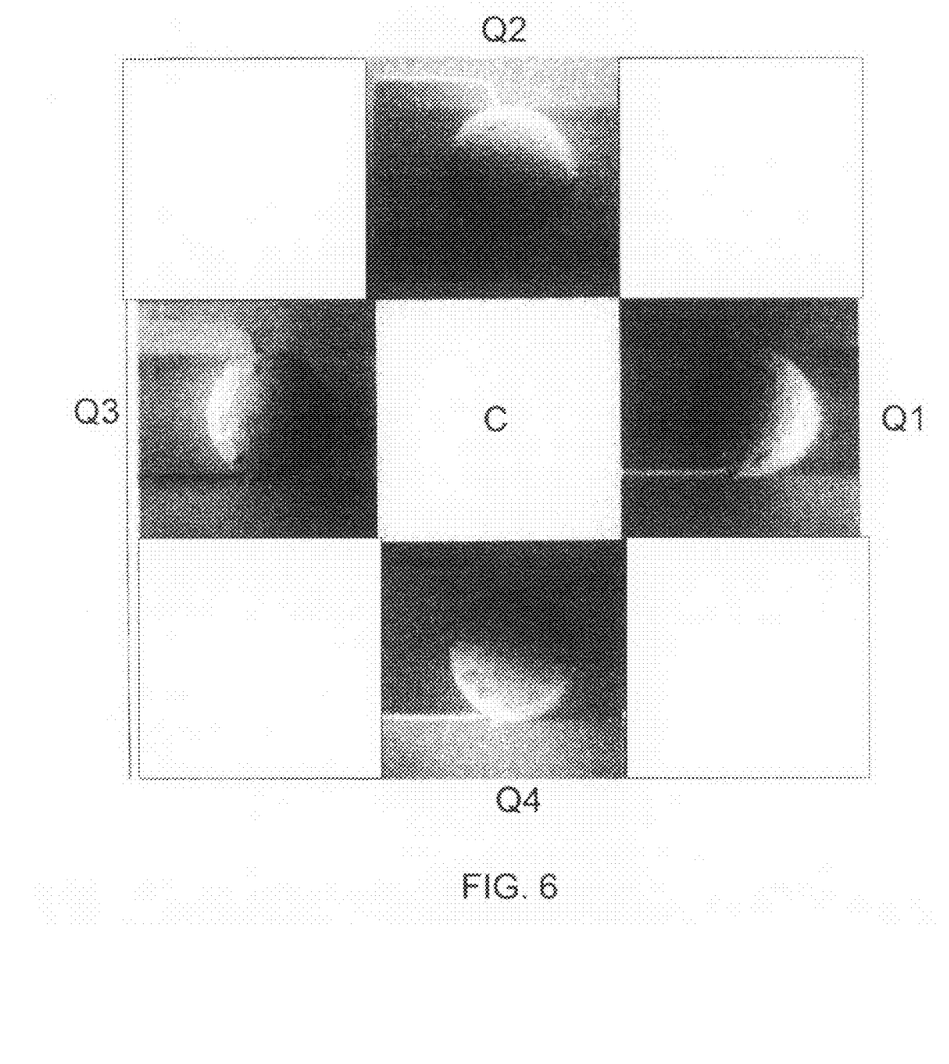
FIG. 6 is a diagram depicting a display layout showing dark field imaging perspectives from four quadrants.

FIG. 6 is a diagram depicting a display layout showing dark field imaging perspectives from four quadrants (Q1, Q2, Q3 and Q4). Each quadrant in the display layout of FIG. 6 may display image data, for example, from a corresponding quadrant of the segmented detector of FIG. 5. The display layout of FIG. 6 allows a user to view four perspectives of an imaged feature at once, each perspective appearing to be "illuminated" from a different side direction.

An additional imaging perspective may be included by adding an image at the center of the display layout (at the location marked "C"). For example, the center in the display layout of FIG. 6 may display bright field image data obtained from a center segment of the segmented detector of FIG. 5. The bright field image provides a perspective of the imaged feature appearing to be "illuminated" from a top or "overhead" direction.

Figure 7:
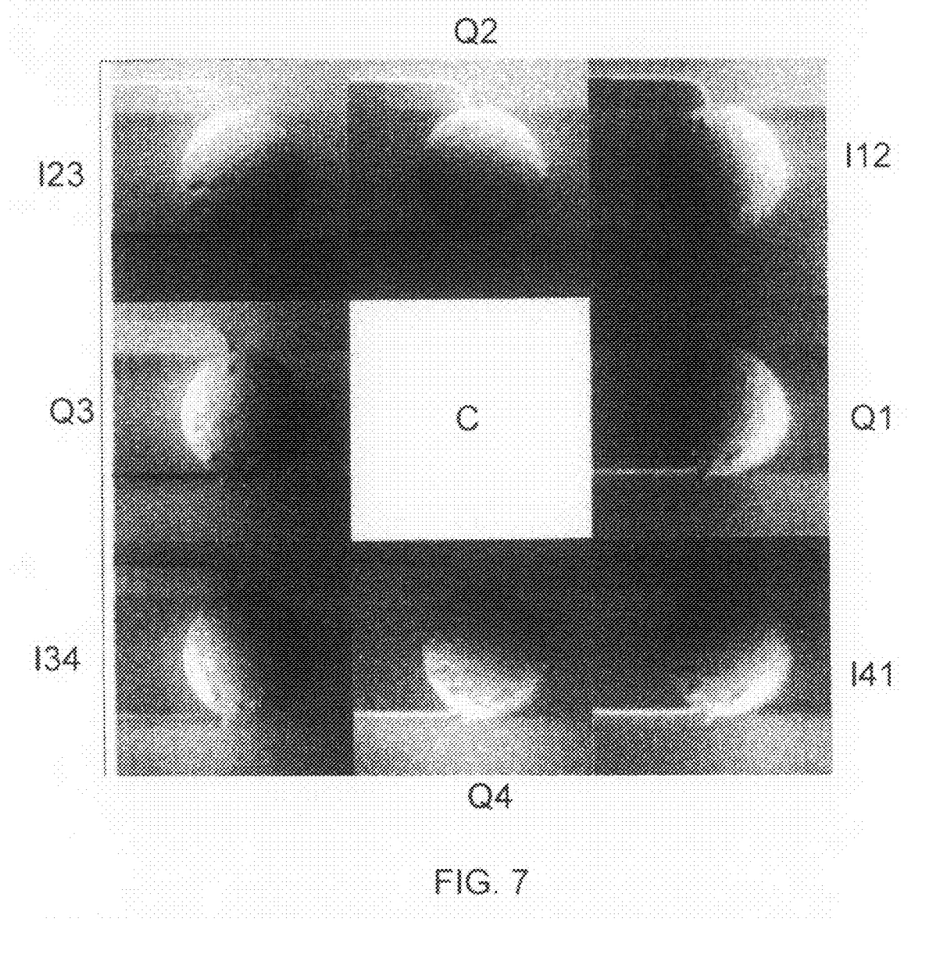
FIG. 7 is a diagram depicting a display layout showing dark field imaging perspectives from four quadrants plus imaging perspectives based on interpolations between the four quadrants in accordance with an embodiment of the invention.

FIG. 7 is a diagram depicting a display layout showing dark field imaging perspectives from four quadrants (Q1, Q2, Q3 and Q4) plus imaging perspectives based on interpolations between the four quadrants in accordance with an embodiment of the invention. The display layout of FIG. 7 allows a user to view eight perspectives of an imaged feature at once, each perspective appearing to be "illuminated" from a different side direction.

The interpolated image marked I12 is an interpolation between the images of the first quadrant Q1 and the second quadrant Q2. The interpolated image marked I23 is an interpolation between the images of the second quadrant Q2 and the third quadrant Q3. The interpolated image marked I34 is an interpolation between the images of the third quadrant Q3 and the fourth quadrant Q4. Lastly, the interpolated image marked I41 is an interpolation between the images of the fourth quadrant Q4 and the first quadrant Q1.

Again, an additional imaging perspective may be included by adding an image at the center of the display layout (at the location marked "C"). For example, the center in the display layout of FIG. 7 may display bright field image data obtained from a center segment of the segmented detector of FIG. 5. The bright field image provides a perspective of the imaged feature appearing to be "illuminated" from a top or "overhead" direction.

FIGS. 6 and 7 show example display layouts with a discrete number of imaging perspectives, including interpolated imaging perspectives in FIG. 7. These embodiments give a user multiple views with which to examine an imaged feature, each view having a different apparent "illumination" angle.

In other embodiments, a user may be provided with a continuum of perspectives with which to examine an imaged feature. This technique effectively interpolates in between the fixed "illumination" angles of the discrete hardware detectors to generate a continuum or near continuum of "illumination" angles. By interpolating between the various dark field images and the bright field image, a continuous range of imaging perspectives may be obtained and displayed.

Figure 8:
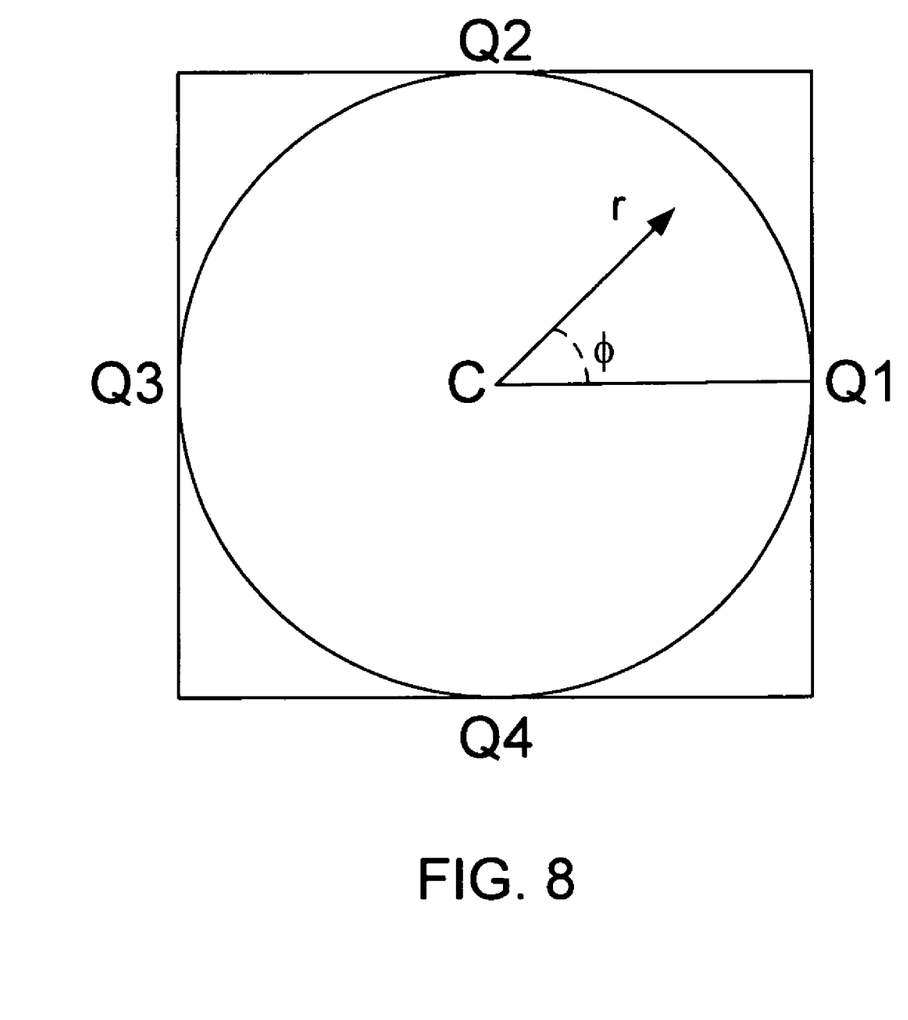
FIG. 8 is a radial diagram which illustrates a representation for controlling a continuum of perspectives in accordance with an embodiment of the invention.

FIG. 8 is a radial diagram which illustrates a representation for controlling a continuum of perspectives in accordance with an embodiment of the invention. The schematic diagram illustrates a representation for a continuous range of dark field (DF) and bright field (BF) imaging perspectives.

More particularly, based on the location in the radial coordinate system $(r, \phi)$ of FIG. 8, the interpolation or mixing between BF and DF imaging perspectives may be determined. First the mixing between dark field channels is performed based on the angle φ, then the mixing between the (mixed) dark field and the bright field channel is performed.

The angle φ determines the mixing or interpolation between the dark field image data from adjacent side channels (Q1, Q2, Q3 and Q4). For example, when φ=0, the dark field image data is entirely (100%) from the Q1 dark field quadrant. When φ=π/2, the dark field image data is entirely (100%) from the Q2 dark field quadrant. When φ=π/2, the dark field image data is entirely (100%) from the Q3 dark field quadrant. When φ=3π/2, the dark field image data is entirely (100%) from the Q4 dark field quadrant. When φ=π/4, the dark field image data is derived half (50%) from the Q1 dark field quadrant and half (50%) from the Q2 dark field quadrant. When φ=3π/4, the dark field image data is derived half (50%) from the Q2 dark field quadrant and half (50%) from the Q3 dark field quadrant. When φ=5π/4, the dark field image data is derived half (50%) from the Q3 dark field quadrant and half (50%) from the Q4 dark field quadrant. When φ=7π/4, the dark field image data is derived half (50%) from the Q4 dark field quadrant and half (50%) from the Q1 dark field quadrant. When φ=π/8, the dark field image data is derived more than half from the Q1 dark field quadrant and less than half from the Q2 dark field quadrant. And so on.

The radial or "reach" variable r determines the interpolation or mixing of the bright field and the dark field imaging perspectives. For example, when r=0, the resulting (interpolated) image is entirely (100%) from the bright field image data from the center channel C. When r=1.0, the resulting (interpolated) image is entirely (100%) from the dark field image data from the outer channels (Q1, Q2, Q3, Q4, or a mixture thereof). When r=0.5, the resulting (interpolated) image is half (50%) from the bright field image data and half (50%) from the dark field image data from the outer channels (Q1, Q2, Q3, Q4, or a mixture thereof). When r=0.75, the resulting (interpolated) image is a quarter (25%) from the bright field image data and three-quarters (75%) from the dark field image data from the outer channels (Q1, Q2, Q3, Q4, or a mixture thereof). Similarly for other r values between 0 and 1.

In one embodiment, the dark channel mixing to create an interpolated dark field signal may be computed using the formula $f=(1-y)*Side1+(y)*Side2$, where $0<=y<=1$ is a piece-wise linear function of the angle φ, and Side1 and Side2 are adjacent dark field channels nearest to the angle φ. For example, if φ is between 0 and π/2, then Side1 is Q1, and Side2 is Q2. if φ is between π/2 and π, then Side1 is Q2, and Side2 is Q3. And so on. Alternatively, instead of y being a piece-wise linear function of the angle φ, y may be a cosine function of φ (i.e. y=cos φ).

After the dark channel mixing is computed, then the bright (center) channel mixing to create a final interpolated signal is computed. In one embodiment, the final interpolated signal may be computed using the formula $g=(1-r)*f+r*Top$, where f is the interpolated dark field signal given above and Top is the bright field channel. Hence, the combined formula may be stated as $g=(1-r)*[(1-y)*Side1+(y)*Side2]+r*Top$.

A user interface is preferably configured for user control of the r and φ variables so as to provide user control of the displayed image perspective. In one embodiment, a cursor control device, such as a joystick, mouse, or trackball may be configured for user control of the r and φ variables. In another embodiment, keys may be used. For example, left and right arrow keys may be used to control the angle φ, and up and down arrow keys may be used to control the radius r.

Figure 9:
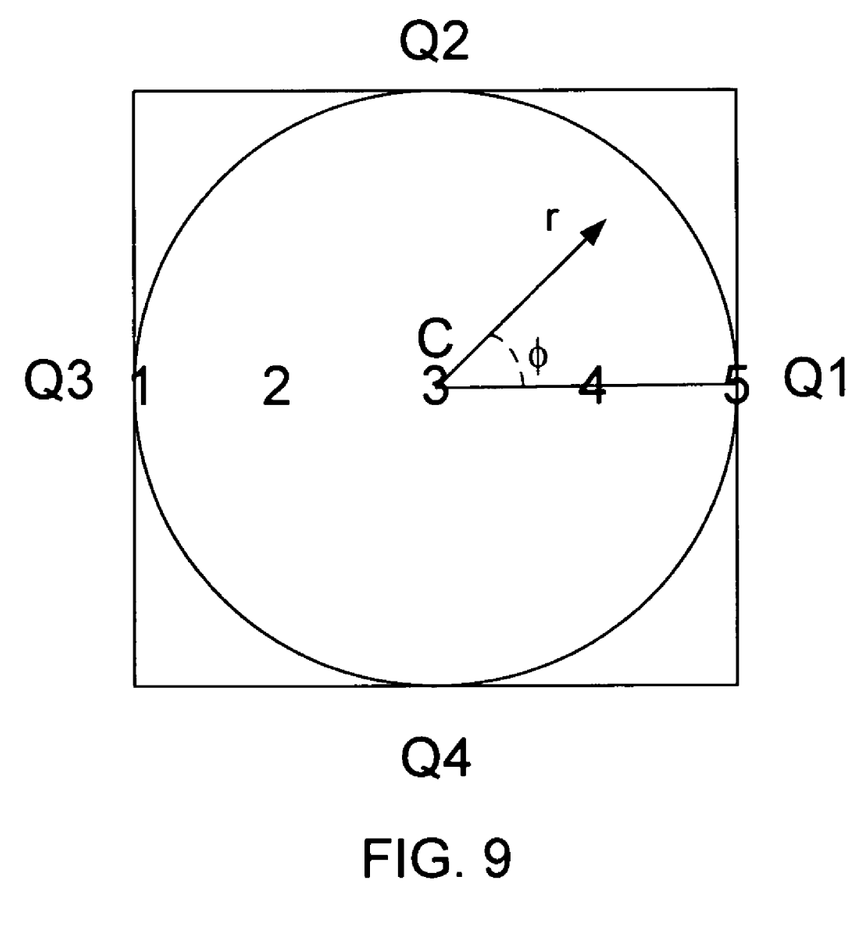
FIG. 9 is a radial diagram showing a first example user navigation between various perspectives in accordance with an embodiment of the invention.

FIG. 9 is a radial diagram showing a first example user navigation between various perspectives in accordance with an embodiment of the invention. In this example, the user navigates along a path going from point 1 to 2 to 3 to 4 to 5. At point 1 (r=1, φ=π), the displayed image is entirely of the dark field image from side channel Q3. At point 2 (r=0.5, φ=π), the displayed image is half from the dark field image from side channel Q3 and half from the bright field image from the center channel C. At point 3 (r=0), the displayed image is entirely from the bright field image from the center channel C. At point 4 (r=0.5, φ=0), the displayed image is half from the dark field image from side channel Q1 and half from the bright field image from the center channel C. Finally, at point 5 (r=1, φ=0), the displayed image is entirely of the dark field image from side channel Q1.

Figure 10:
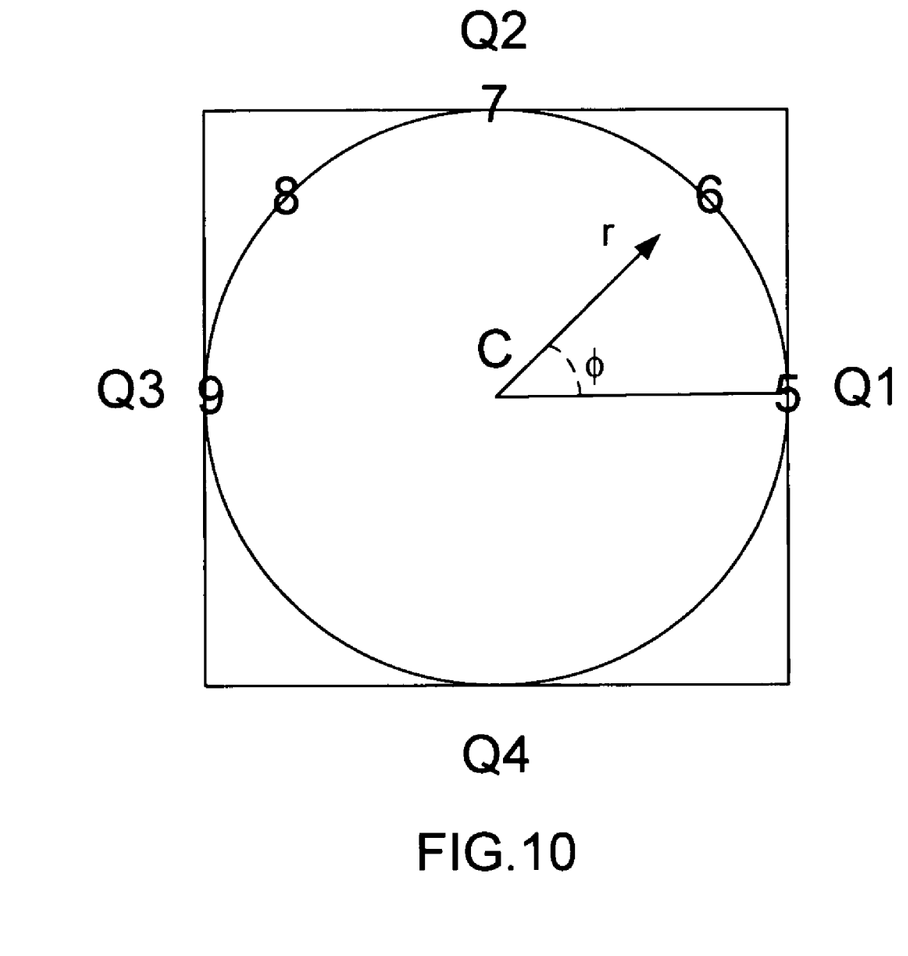
FIG. 10 is a radial diagram showing a second example user navigation between various perspectives in accordance with an embodiment of the invention.

FIG. 10 is a radial diagram showing a second example user navigation between various perspectives in accordance with an embodiment of the invention. At point 5 (r=1, φ=0), the displayed image is entirely of the dark field image from side channel Q1. At point 6 (r=1, φ=π/4), the displayed image is half from the dark field image from side channel Q1 and half from the dark field image from the side channel Q2. At point 7 (r=1, φ=π/2), the displayed image is entirely from the dark field image from the side channel Q2. At point 8 (r=1, φ=3π/2), the displayed image is half from the dark field image from side channel Q2 and half from the dark field image from the side channel Q3. Finally, point 9 (r=1, φ=π), the displayed image is entirely of the dark field image from side channel Q3.

The present application discloses a function and technique to allow a user to quickly determine a desired view from multiple SEM images, including but not limited to dark field (DF) and bright field (BF) images. This is accomplished by providing a continuous or nearly continuous range of imaging perspectives using interpolation between fixed perspectives. As described above, the function and technique described herein "interpolates" illumination angles in between fixed hardware detector illumination angles. In addition to "side" illumination angle, the user is able to select the amount of "top" illumination by selecting an amount of bright field information to be mixed in.

Advantageously, this function and technique may be utilized for situations where the optimum view angle is not known beforehand. For example, shallow scratches on a substrate will have more or less contrast in an SEM dark field image depending upon the slope of the edge, the depth, and the orientation with respect to the dark field detectors. This function may allow an automated system to compare a reference image to a defect image through a continuous range of side illumination angles (for example, from 0 to 360 degrees). In addition, an automated routine may be configured to select a "best" imaging perspective and present the user with a single image with the selected imaging perspective.

Furthermore, this function and technique may be used to facilitate automated or manual defect classification by (i) reducing the amount of information an operator must digest, (ii) providing an optimized image based on perspective, and/or (iii) reducing confusion surrounding the "innie" (concave) or "outie" (protruding) defect classification. Regarding the "innie" or "outie" defect classification, one DF detector may provide image data indicating that a defect is an "outie", while another DF detector in a different orientation may show the defect as being an "innie". The multitude of imaging perspectives provided by the presently disclosed function and technique gives a source of useful data to determine the correct defect classification.

This function and technique may be performed using software code with computer-readable instructions stored in a memory system and executable on one or more processors. Alternatively, this function and technique may be performed using hardware circuitry to perform analog signal processing between the multiple channels.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method of imaging using an electron beam; the method comprising:
   focusing an incident electron beam onto the specimen surface;
   extracting a scattered electron beam from the specimen surface;
   detecting a plurality of dark field signals using a detection system; and
   generating an interpolated dark field signal using the plurality of dark field signals.

2. The method of claim 1, further comprising:
   detecting a bright field signal using the detection system; and
   generating a final interpolated signal using the interpolated dark field signal and the bright field signal.

3. The method of claim 1, wherein the incident electron beam is scanned over an area of the specimen surface, and the detection system stores detected signals in synchronization with said scanning.

4. The method of claim 1, wherein the scattered electron beam comprises secondary electrons.

5. The method of claim 1, further comprising:
   receiving user input which determines a degree of interpolation between two adjacent dark field signals so as to generate the interpolated dark field signal.

6. The method of claim 2, further comprising:
   receiving user input which determines a degree of interpolation between two adjacent dark field signals so as to generate the interpolated dark field signal and an amount of interpolation between the interpolated dark field signal and the bright field signal so as to generate a final interpolated signal.

7. The method of claim 6, wherein the user input is received from a cursor control device.

8. The method of claim 2, wherein the degree of interpolation between two adjacent dark field signals is representable by an angular variable which varies from 0 to $2\pi$, and the amount of interpolation between the interpolated dark field signal and the bright field signal is representable by a radial variable which varies from 0 to 1.

9. A scanning electron beam apparatus comprising:
   an objective lens configured to focus an incident electron beam onto a specimen surface and to extract a scattered electron beam therefrom;
   scan deflectors configured to deflect the incident electron beam so as to scan the incident electron beam over the specimen surface;
   de-scan deflectors configured to deflect the scattered electron beam so as to compensate for the scanning of the incident electron beam;
   an energy-filter drift tube positioned to receive the scattered electron beam after the de-scan deflectors;
   a segmented detector positioned to receive the scattered electron beam after the energy-filter drift tube and to detect a plurality of dark field signals; and
   an image processing system configured to generate an interpolated dark field signal using the plurality of dark field signals.

10. The apparatus of claim 9, wherein the image processing system is further configured to detect a bright field signal using the detection system and to generate a final interpolated signal using the interpolated dark field signal and the bright field signal.

11. The apparatus of claim 9, wherein the incident electron beam is scanned over an area of the specimen surface, and the detection system stores detected signals in synchronization with said scanning.

12. The apparatus of claim 9, wherein the scattered electron beam comprises secondary electrons.

13. The apparatus of claim 9, further comprising:
    a user control for determining a degree of interpolation between two adjacent dark field signals so as to generate the interpolated dark field signal.

14. The apparatus of claim 10, further comprising:
    a user control for determining a degree of interpolation between two adjacent dark field signals so as to generate the interpolated dark field signal and an amount of interpolation between the interpolated dark field signal and the bright field signal so as to generate a final interpolated signal.

15. The apparatus of claim 14, wherein the user control comprises a cursor control device.

16. The apparatus of claim 10, wherein the degree of interpolation between two adjacent dark field signals is representable by an angular variable which varies from 0 to $2\pi$, and the amount of interpolation between the interpolated dark field signal and the bright field signal is representable by a radial variable which varies from 0 to 1.

17. The method of claim 1, wherein the plurality of dark field signals are detected from the scattered electron beam by the detection system.

18. The method of claim 17, wherein each of the plurality of dark field signals corresponds to an outer segment of the detection system.

19. The method of claim 18, further comprising:
    detecting a bright field signal from the scattered electrons by the detection signal, wherein the bright field signal corresponds to a central segment of the detection system.

20. The apparatus of claim 9, wherein the segmented detector comprises a plurality of outer segments which are configured to detect the plurality of dark field signals and a central segment which is configured to detect the bright field signal.

\* \* \* \* \*